United States Patent [19]
Whittington et al.

[11] Patent Number: 5,811,664
[45] Date of Patent: Sep. 22, 1998

[54] DEBRIS MONITORING

[75] Inventors: Herbert William Whittington, Longniddry; Brian William Flynn, Edinburgh, both of United Kingdom

[73] Assignee: University of Edinburgh, Edinburgh, United Kingdom

[21] Appl. No.: 793,523
[22] PCT Filed: Aug. 31, 1995
[86] PCT No.: PCT/GB95/02047
  § 371 Date: Feb. 27, 1997
  § 102(e) Date: Feb. 27, 1997
[87] PCT Pub. No.: WO96/07090
  PCT Pub. Date: Mar. 7, 1996

[30] Foreign Application Priority Data

Aug. 31, 1994 [GB] United Kingdom .................... 9417763

[51] Int. Cl.⁶ .................................................. G01R 33/12
[52] U.S. Cl. .......................................... 73/53.07; 324/204
[58] Field of Search ............................... 73/53.07, 61.42; 324/204; 340/631, 627

[56] References Cited

U.S. PATENT DOCUMENTS

| | | |
|---|---|---|
| 3,744,044 | 7/1973 | Vosteen . |
| 4,439,734 | 3/1984 | Weber . |
| 4,837,511 | 6/1989 | Whittington et al. . |
| 4,926,120 | 5/1990 | Veronesi et al. . |
| 5,315,243 | 5/1994 | Kempster et al. . |

FOREIGN PATENT DOCUMENTS

| | | |
|---|---|---|
| 576862 | 8/1924 | France . |
| 2284891 | 6/1995 | United Kingdom . |

OTHER PUBLICATIONS

"An On–Line Wear Debris Monitor" Measurement Science and Technology, vol. 3, No. 7, Jul. 1992, Bristol GB, pp. 656–661 (H.W. Whittington, et. al.).

*Primary Examiner*—Robert Raevis
*Attorney, Agent, or Firm*—Young & Basile, P.C.

[57] ABSTRACT

A sensor for use in machine wear debris monitoring transducers which detect metallic particles present in a flow of fluid, such as lubricating oil. The sensor comprises an inductive coil having a plurality of turns for surrounding a non-magnetic conduit. An electrically conducting screen is located between the coil and the flow of fluid, the coil being electrically insulated from the screen, so as to isolate capacitatively the contents of the conduit from the coil. The resonant frequency of a tank circuit incorporating the sensor is thus unaffected by changes in the dielectric properties of the contents of the conduit caused by air bubbles and/or water droplets in the flow of fluid. The screen may be a single turn of thin metal foil having a gap between adjacent ends, or a mesh, or a metallic coating sprayed onto the conduit.

18 Claims, 3 Drawing Sheets

DEBRIS MONITORING

This invention relates to machine wear debris monitoring and, in particular, to transducers for use in monitoring machine wear debris. More specifically, the invention concerns an improved sensor for such transducers.

There is considerable interest in developing accurate and reliable techniques for continuous, "on-line" monitoring of metallic particles in the lubricating oil of machines such as engines and gear boxes. Such metallic particles are produced by mechanical wear in the machines and the presence of metallic wear particles can indicate incipient machine failure. The rate at which wear debris is generated can be used as a measure of the condition of a machine.

Wear debris monitoring transducers are known which utilise an inductive coil having a plurality of turns which are wound around a non-magnetic pipe containing a lubricant stream. As metallic particles in the lubricant pass through the coil they are magnetically coupled to the coil.

Ferrous particles have a high relative permeability and so a ferrous particle passing through the coil will increase the inductance of the coil. Non-ferrous metallic particles will decrease the inductance due to eddy currents which are induced in the particles by the magnetic field of the inductive coil. By resonating the inductive coil with a fixed capacitor in the resonant or tank circuit of an oscillator it is possible to monitor changes in the coil inductance as changes in the frequency of the oscillator since the resonant frequency of the tank circuit is dependent upon the inductance of the coil. An increase in the coil inductance will cause a decrease in the oscillator frequency indicating the presence of ferrous particles. A decrease in inductance will cause an increase in the oscillator frequency, indicating the presence of non-ferrous metallic particles. The magnitude of the frequency change can be used to indicate the size of a metallic particle in the lubricating fluid passing through the coil.

In practice most such transducers are used in systems where the lubricating fluid stream contains air bubbles or water droplets. This is a common phenomenon in lubrication systems and pumped lubrication systems in particular may include significant amounts of foam within the fluid (air content may be in excess of 50%), as well as lubricating fluid which has become contaminated with water. The inductive coil of the transducer has a parasitic capacitance arising from stray capacitance effects between adjacent turns of the coil. Where the coil is placed around a relatively thin-walled pipe this parasitic capacitance will be affected by the dielectric properties of the contents of the pipe. Since the relative permittivities of air, oil and water are approximately unity, two point five, and eighty-one respectively, the parasitic capacitance of the coil may vary considerably as air or water droplets present in the lubricating oil or fluid pass through the coil. As the resonant frequency of the oscillator tank circuit is dependent on capacitance as well as inductance, changes in the capacitance of the coil result in changes in the resonant frequency. An increase or decrease in capacitance will result in a decrease or increase, respectively, in the resonant frequency. Thus the responses of the transducer to air bubbles and water droplets will be similar to those cause by metallic particles. This can lead to unreliable results and undesirable machine "down-time" due to false alarms and may lead in time to the monitor being deliberately inactivated as a result of user frustration with repeated false alarms, with the potentially highly dangerous consequence of the engine or gearbox being left without any means for indicating failure. Moreover, turbulent flow containing trapped air or foam will give a continuous noisy output signal from the transducer which may mask signals from metallic debris.

A probe member for a machine wear debris monitoring transducer is described in U.S. Pat. No. 5,041,856 which attempts to overcome the problems associated with stray capacitance effects in the transducer coil. The probe member consists of an inductor which consists of a single turn electric conductor wrapped around a fluid passage through which lubricating fluid flows. The inductor incorporates marginal end portions between which is located dielectric material to form a capacitor, the probe member and the capacitor forming a tank circuit. The capacitance of the probe member is sufficiently high largely to swamp any changes in capacitance due to changes in the permittivity of the contents of the fluid passage. As a result of having only a single turn inductor, however, the inductance of the probe is generally reduced in comparison to multi turn coil systems, thus resulting in a substantial loss in sensitivity.

It is an aim of the present invention to avoid or reduce one or more of the aforementioned disadvantages of the known transducers.

According to a first aspect, the present invention provides a sensor for use in detecting metallic particles carried by a fluid flowing through a fluid passage inside a substantially non-magnetic conduit, the sensor comprising an inductive coil having a plurality of turns for surrounding said fluid passage in use of the sensor so as to couple magnetically the coil to any metallic particles carried by the fluid flowing through the conduit, wherein is provided a screen of electrically conductive material between said fluid passage and the inductive coil, the coil being electrically insulated from the screen, and the screen being formed and arranged so as to substantially isolate capacitatively the fluid passage contents from the coil.

The sensor of the present invention thus has the advantage of substantially preventing the fluid passage contents from contributing to the capacitance of the inductive coil. The coil has a parasitic capacitance due to capacitance between adjacent turns, as well as capacitance between the coil and the earthed screen, but the capacitance is effectively held or clamped at a substantially constant value. Thus, when the sensor is incorporated in a debris monitoring transducer, the changes in resonant frequency of the tank circuit will be due substantially only to changes in inductance caused by metallic particles in the fluid passage, the sensor being substantially unaffected by the presence of air bubbles or water droplets in lubricating fluid in the fluid passage inside the conduit.

Preferably, the screen is electrically earthed. Alternatively, the screen may be set at an appropriate voltage. The latter case provides "active" screening of the inductive coil. The appropriate voltage is preferably such that the potential difference between the inductive coil and the screen is substantially constant.

Where such "active" screening is employed, said voltage may be taken from an electronic circuit of a debris monitoring transducer system in which the sensor may be incorporated. This technique follows the principle of a "guard shield" as described in relation to differential amplifiers in the book entitled "Noise Reduction Techniques in Electronic Systems" by Henry W. Ott, published by John Wiley & Son, 1976.

Preferably the screen is made of a non-magnetic material. The screen may generally comprise a more or less thin metallic sheet, which may be apertured, e.g. so as to form a mesh, and which forms a generally tubular member which may extend around an outer surface of the conduit or, preferably, extends substantially over an inner surface of the conduit, surrounding the fluid passage means. The screen performs the function of a so-called Faraday screen which electrostatically shields the inductor coil turns from the dielectric constituted by the contents of the conduit fluid passage.

In the case of a screen comprising a substantially continuous foil or the like, this is preferably provided with at least one gap which extends generally parallel to the axis of the coil and between opposed end portions of the foil. The gap functions substantially to prevent such currents as would tend to be induced by the magentic field of the inductor coil from flowing freely in the screen. A screen which formed a single complete turn would have the effect of a shorted turn which would act as a secondary coil coupled to the multiturn inductor coil, resulting in energy loss to the second coil and consequently greatly reduced sensitivity of the transducer.

The screen is generally of an electrically conductive non-magnetic metal such as copper, aluminium, silver, gold etc. through other materials such as electrically conductive plastics could also be used. Conveniently the screen is in the form of a thin foil. The screen could also be formed by spraying, plating or otherwise depositing a thin film of metallic paint, or other electrically conductive material, onto the outer surface of the conduit prior to winding the inductor coil around the conduit. Another possibility would be to spray the interior surface of the conduit with a metallic coating.

The screen may also be in the form of a mesh of metallic or electrically conductive material. The advantage of a mesh screen is a reduction in induction losses in the coil due to eddy currents produced in the screen—the open areas of the mesh would act to minimise such eddy currents. The mesh may extend fully around the fluid passage means, or may be provided with a gap between end portions of the mesh. The mesh may conveniently comprise a thin metal foil permeated with microscopic holes, sometimes referred to as "microfoil".

Preferably, the sensor and the non-magnetic conduit are provided as an integral unit. This makes the sensor easier to install in "on-line" working locations where the sensor may be retrofitted to existing lubrication systems. Alternatively, the sensor unit may be installed in a by-pass loop taken off from the main lubricating fluid flow pipework of the machine in which the sensor is being used.

The inductive coil may be provided integrally in a wall of the conduit. In this arrangement, the screen of electrically conducting material is preferably provided on an inner surface of the conduit, between the coil and the fluid passage, and a protective layer of non-conducting, non magnetic material is provided to protect the screen from impact damage due to sharp metallic particles in the lubricating fluid. The associated electronic circuitry may conveniently be mounted inside the wall of the conduit, although where the sensor is to be installed in a high temperature environment this may be less appropriate.

It will be appreciated that the screen will result in some loss of sensitivity. By using a relatively thin foil or film (e.g. from 5 to 20 $\mu$m thickness) and/or providing apertures therein, the loss of sensitivity may be made quite small e.g. a factor of 2 or less. On the other hand a reduction in signal noise due to the presence of air bubbles or water droplets of 100 times or more may be achieved in some cases, thereby substantially reducing the risk and incidence of false alarms.

According to a second aspect, the invention provides an apparatus for detecting metallic particles carried by a fluid flowing through a conduit, including an oscillator having a resonant circuit including a capacitor and a sensor according to the first aspect of the invention, the oscillator being such that the frequency of its oscillation is dependent upon the inductance of the inductive coil, and measurement means being provided for measuring changes in the oscillator frequency due to changes in the inductance of the coil resulting from magnetic coupling of the coil to metallic particles carried by fluid flowing through the conduit.

Some suitable circuitry which could be used is described in more detail in U.S. Pat. No. 4,837,511.

Alternatively, and preferably, the measurement means comprises electronic circuit means including a phase-locked loop for detecting changes in frequency of the oscillator. The oscillator preferably comprises a voltage controlled oscillator (VCO) in which the inductive coil provides the resonating inductor and which is held in the phase-locked loop with a crystal-controlled reference oscillator.

The frequency response of the phase-locked loop is set to enable disturbances in frequency produced by metallic particles passing through the inductor of the VCO to be detected. Additionally, the phase-locked loop maintains long-term frequency stability of the VCO by compensating for any frequency drift induced by temperature changes in the surrounding environment.

The improved reliability of the sensor and apparatus according to the invention makes the use of on-line machine wear debris monitoring transducers more attractive for use in critical environments such as ship and helicopter gear boxes, where false alarms produced by prior known transducers were costly and undesirable. The sensor and the apparatus incorporating the sensor are, however, also suitable for use in a range of other applications including on-line monitoring of metallic particle contamination in food production lines and ferrous particle contamination in glazing fluid commonly sprayed onto articles in large-scale pottery concerns (such contamination leads to cosmetically unattractive rust streaks upon firing of the glazed articles). In fact, the sensor and apparatus could be used in any application where monitoring and reliable detection of metallic particles in fluid flow is required.

Preferred embodiments of the invention will now be described by way of example only and with reference to the accompanying drawings in which.

Figure 1:
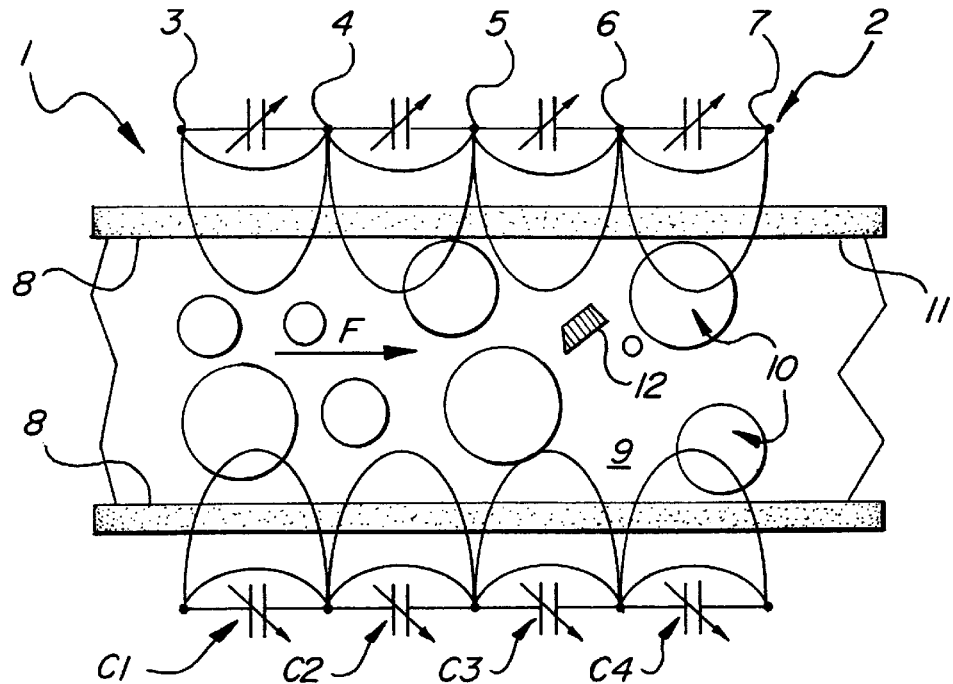
FIG. 1 is a cross-sectional side view of a sensing head of a known debris monitoring transducer system.

FIG. 1 illustrates a known sensor head 1 for use in a machine wear debris monitoring transducer system. The sensor head comprises an inductive coil 2 having a plurality of turns 3, 4, 5, 6, 7 which surround a pipe 8 made of electrically insulating, non-magnetic material. A stream of lubricating oil 9 flows through a fluid passage 11 defined within the pipe in a direction F and contains a number of air bubbles and/or water droplets 10 and one or more metal particles 12. As the metal particle(s) 12 pass through the coil, the inductance of the coil changes. Between each two adjacent turns of the coil 2 a variable stray capacitance C1, C2, C3, C4 exists.

As illustrated in FIG. 1, each capacitance C1, C2, C3, C4 at any given time is dependent upon permittivity of the contents of the pipe at that time. Due to the different permittivities of oil (approx. 2.5), air (approx. 1.0) and water (approx. 81), the stray capacitances are thus dependent upon the presence and amount of air bubbles or water droplets present in the oil in the pipe. (In pumped lubrication systems, the air content is often well in excess of 50%).

Figure 2:
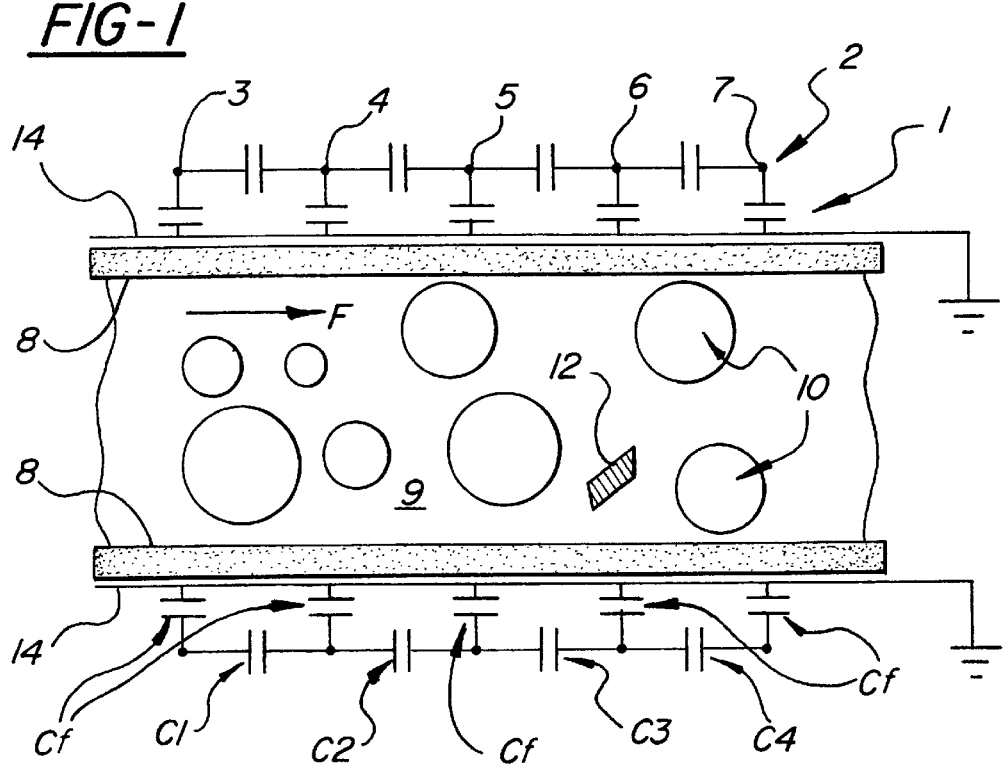
FIG. 2 is a cross-sectional side view of one embodiment of a sensor head according to the present invention.
Figure 3:
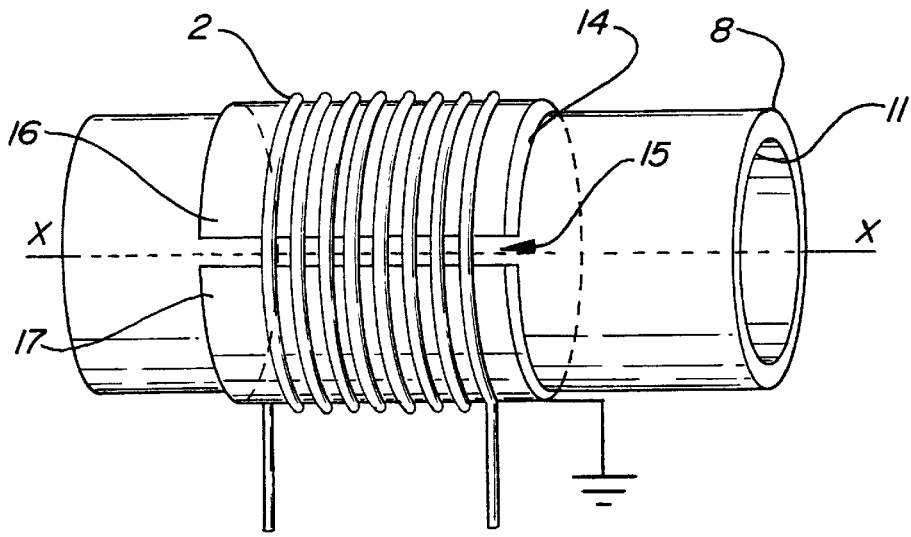
FIG. 3 is a perspective view of a sensor head similar to that shown in FIG. 2.

The sensor head 1 shown in FIG. 2 substantially eliminates variation in the stray capacitances C1, C2, C3, C4 due to the changing dielectric properties of the contents of the pipe 8. Identical reference numerals are used to identify like parts to those shown in the sensor of FIG. 1. The coil 2 comprises a copper wire coated in insulating material. In addition to the pipe 8 and the coil 2, the sensor further comprises a screen 14 which consists of a single turn of non-magnetic metal foil, such a copper, placed around the pipe 8, between the pipe and the coil 2 in such a way that it forms an "open-circuited" turn. FIG. 3 shows a sensor which is like that of FIG. 2 but which includes an additional number of turns in the inductive coil 2. As shown clearly in FIG. 3, a gap 15 is provided between two end portions 16, 17 of the screen 14. The gap extends generally parallel to the axis X of the coil. The gap acts to prevent the flow of induced currents in the screen, such currents tending to be induced by the magnetic field of the coil 2 when an alternating current is passed through the coil. The gap thus prevents the screen acting as a secondary inductor. As long as the screen is an open circuit and does not constitute a shortened turn, it will thus not shield the magnetic field of the coil by allowing induced currents to flow round the screen. Some eddy currents may nevertheless be induced in the screen by the coil, but these will produce only a relatively small, fixed (i.e. non-varying) decrease in the coil inductance.

The screen 14 is electrically earthed, as shown in FIGS. 2 and 3. In an alternative embodiment, a voltage signal is applied to the screen.

In either embodiment, the screen acts as an electrostatic screen, in the manner of a Faraday screen, to ensure that the stray capacitance between each two adjacent turns of the coil, and thus the total capacitance of the coil, remains constant regardless of the dielectric contents of the pipe. The screen achieves this effect by defining a fixed capacitance CF between the coil turns and ground. Moreover, the stray capacitance C1, C2, C3, C4 between each two adjacent turns is fixed at a constant value. The total capacitance of the coil 2 is thus unaffected by the dielectric contents of the pipe. However, the magnetic properties of the contents of the pipe still influence the coil inductance and changes in inductance produced by metallic particle(s) 12 in the oil 9 are still easily detectable.

By incorporating the sensor head into the necessary electronic circuitry it is now possible to construct a debris monitoring transducer which will respond to magnetic changes in the coil caused by metallic debris particles and not changes in coil capacitance due to air bubbles, water droplets, or other non-metallic debris present in the lubricating oil passing through the pipe 8.

Figure 6A:
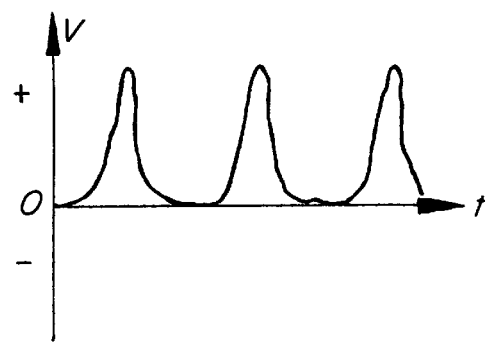
FIG. 6(a) is a schematic qualitative illustration of a signal taken from the circuit of FIG. 4 where a ferrous metallic particle has been passed repeatedly through the sensor head.
Figure 6B:
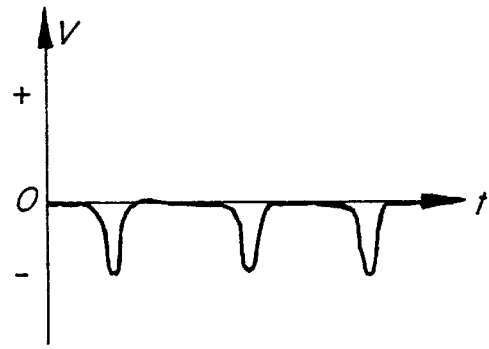
FIG. 6(b) is a schematic qualitative illustration of the same signal where a non-ferrous metallic particle has been passed repeatedly through the sensor head.
Figure 4:
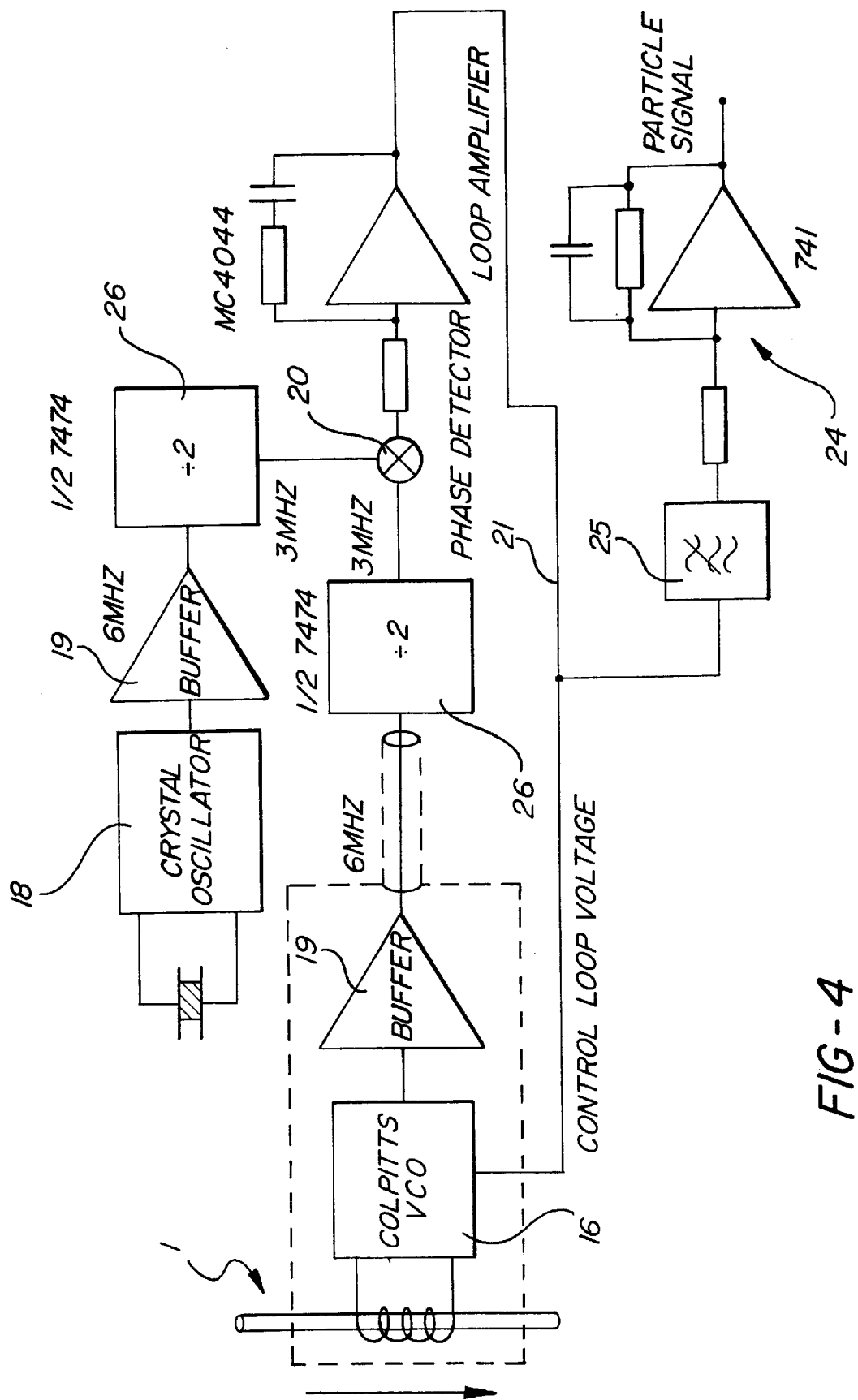
FIG. 4 is a schematic illustration of an electronic circuit incorporating the sensor head of FIGS. 3 or 4.

FIG. 4 shows a suitable circuit for detecting changes in inductance of the coil 2. The sensor 1 (screen 14 not shown), is utilised as the resonating inductor, resonating with a fixed capacitor, in a Colpitts voltage controlled oscillator (VCO) 16 using a common collector bipolar transistor and having a frequency output of approx. 6 MHz. The VCO and sensor together constitute a transducer which converts changes in inductance of the coil 2 into changes in resonant frequency of the resonant circuit of the oscillator 16. The transducer is incorporated in a phase-locked loop 21 with a 6 MHz quartz crystal reference oscillator 18. The outputs of the VCO 16 and crystal oscillator 18 are buffered 19, divided by two 26, and input to a phase detector 20 (Motorola MC4044) which incorporates a control loop amplifier. Any detected phase difference results in an error signal being generated, the error signal being fed back as a control loop voltage to the VCO to hold the VCO in phase lock with the reference oscillator 18. Changes in the inductance of the coil due to metallic particles result in frequency changes in the oscillator and consequent phase differences between the VCO output and the crystal oscillator. By monitoring the error signal fed back to the VCO it is possible to detect the presence and type of metallic particles present. As the control voltage signals corresponding to metallic particles are relatively small (the change in inductance of the sensor coil due to wear debris particles typically being around one part in $10^4$–$10^5$), the signals are amplified and filtered in a three stage amplifier 24, 25 to improve the signal to noise ratio. FIGS. 6(*a*) and (*b*) show schematically two qualitative graphs of the error signal voltage V plotted against time t for a ferrous and non-ferrous particle respectively, the direction of the signal peaks indicating whether the particle is ferrous or non-ferrous.

By utilising frequencies in the range of approx 6–10 MHz it is possible to utilise standard printed circuit technology. The VCO and sensor head 1 may be mounted in a grounded metal box and the rest of the electronics may be mounted remotely if unfavourable temperature conditions exist around the sensor area. The screen may be of a 10 $\mu$m thick copper foil. Alternatively, it is possible that a copper mesh screen could be used, or a metal coating could be sprayed onto the outer surface of the pipe 8. In all the embodiments, the coil is a copper wire having an insulating coating.

In the embodiment where a voltage signal is applied to the screen, this voltage is taken from the VCO oscillator output. In this way the screen voltage "tracks" the VCO output voltage and the potential difference between the screen and the coil is maintained substantially constant.

Figure 5:
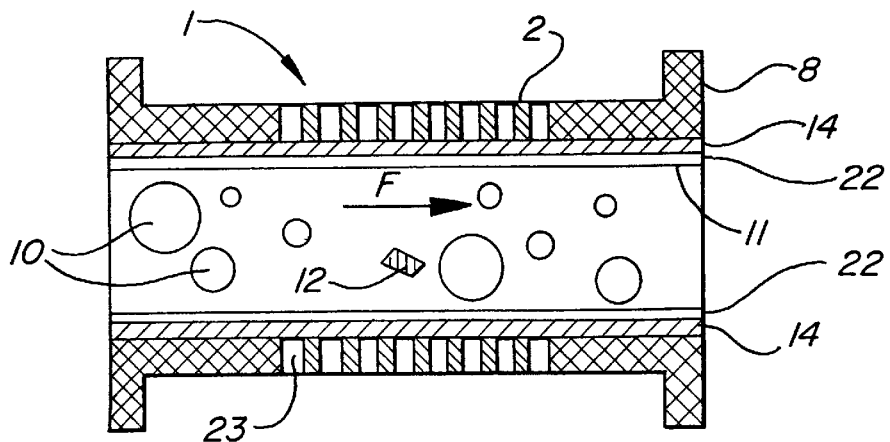
FIG. 5 is a cross-sectional side view of another embodiment of the sensor head according to the present invention.

FIG. 5 shows an alternative sensor embodiment where the coil 2 is incorporated in a wall 23 of a pipe section 8 which has an inner coating of copper foil sandwiched between an inner surface of the pipe and a protective layer 22 of plastics material. The entire sensor 1 thus comprises a single pipe section unit, with no protruding coil or foil edges, which may be easily retrofitted to the pipework of the lubrication system to be monitored.

The described transducer system enables metallic particles to be reliably detected, avoiding undesirable false alarms associated with prior known systems which were greatly influenced by the dielectric properties of the contents of the pipe. The improved sensor herein described has slightly reduced sensitivity as compared with sensors not incorporating the screen 14. However, the much increased reliability of the sensor makes it much more attractive for real applications. Nevertheless, metallic particles of about 70 $\mu$m to 100 $\mu$m diameter and upwards can be detected using the transducer system incorporating the improved sensor, with an inductive coil diameter of approximately 6 mm. Larger or smaller coil diameters could be used; these will vary the sensitivity of the coil to changes in inductance.

Signal integration methods and/or signal averaging methods may be used on the control loop voltage signal to monitor the size and number of metallic particles passing through the coil over a predetermined period of time. In this way the level of machine wear can be accurately monitored.

We claim:

1. A sensor for use in detecting metallic particles carried by a fluid flowing through a fluid passage inside a substantially non-magnetic conduit, the sensor comprising an inductive coil having a plurality of turns for surrounding said fluid passage in use of the sensor so as to couple magnetically the coil to any metallic particles carried by the fluid flowing through the conduit, wherein a screen of electrically conductive material is provided between said fluid passage and the inductive coil, the coil being electrically insulated from the screen, and the screen being formed and arranged so as to substantially isolate capacitatively the fluid passage contents from the coil.

2. A sensor according to claim 1, wherein the screen is electrically earthed.

3. A sensor according to claim 1, wherein a voltage signal is applied to the screen.

4. A sensor according to claim 3, wherein the screen is set at an appropriate voltage such that the potential difference between the screen and the inductive coil is substantially constant.

5. A sensor according to claim 1, wherein the electrically conductive material of the screen is non-magnetic.

6. A sensor according to claim 1, wherein the screen comprises a metallic sheet of foil.

7. A sensor according to claim 6, wherein the screen comprises a thin sheet of copper foil.

8. A sensor according to claim 1, wherein the screen comprises a film of electrically conductive material sprayed onto the conduit.

9. A sensor according to claim 1, wherein the screen comprises an electrically conducting mesh.

10. A sensor according to claim 9, wherein the mesh comprises a metal foil, or film, which is permeated with microscopic holes.

11. A sensor according to claim 1, wherein the screen (14) forms a generally tubular member which extends substantially around an outer surface of the conduit (8).

12. A sensor according to claim 1, wherein the screen (14) extends substantially over an inner surface of the conduit (8).

13. A sensor according to claim 12 when mounted in or on a said non-magnetic conduit (8).

14. A sensor according to claim 13 which sensor is formed integrally with said conduit.

15. A sensor according to claim 14, as dependent from claim 12, wherein the screen (14) is provided on an inner surface of the conduit, between the coil (2) and a protective layer (22) of non-conducting, non-magnetic material which defines the fluid passage (11) inside the conduit (8).

16. An apparatus for detecting metallic particles carried by a fluid (9) flowing through a conduit, and including an oscillator (16) having a resonant circuit including a capacitor and a sensor (1) according to claim 15, the oscillator being such that the frequency of its oscillation is dependent upon the inductance of the inductive coil (2), and measurement means (18, 20, 21) being provided for measuring changes in the oscillator frequency due to changes in the inductance of the coil resulting from magentic coupling of the coil to metallic particles (12) carried by fluid flowing through the conduit (8).

17. An apparatus according to claim 16, wherein the measurement means comprises electronic circuit means including a phase-locked loop (21) for detecting changes in frequency of the oscillator.

18. An apparatus for detecting metallic particles carried by a fluid flowing through a conduit, and including an oscillator having a resonant circuit including a capacitor and a sensor according to claim 4, the oscillator being such that the frequency of its oscillation is dependent upon the inductance of the inductive coil, and measurement means, being provided for measuring changes in the oscillator frequency due to changes in the inductance of the coil resulting from magnetic coupling of the coil to metallic particles carried by fluid flowing through the conduit, and wherein said voltage at which the screen is set is taken from an output of the oscillator.

* * * * *

UNITED STATES PATENT AND TRADEMARK OFFICE
CERTIFICATE OF CORRECTION

PATENT NO. : 5,811,664
DATED : September 22, 1998
INVENTOR(S) : Herbert William Whittington and Brian William Flynn It is certified that error appears in the above-identified patent and that said Letters Patent is hereby corrected as shown below:

Column 7, line 18, after "coil" insert --, wherein the screen is provided with at least one gap which extends generally parallel to an axis of the coil and between opposed end portions of the screen--.

Signed and Sealed this

Twenty-ninth Day of May, 2001

*Attest:*

NICHOLAS P. GODICI

*Attesting Officer*     *Acting Director of the United States Patent and Trademark Office*